United States Patent
Karim et al.

(10) Patent No.: US 9,636,663 B2
(45) Date of Patent: May 2, 2017

(54) HIGH PRODUCTIVITY CATALYST FOR ALKANE OXIDATION TO UNSATURATED CARBOXYLIC ACIDS AND ALKENES

(71) Applicant: SAUDI BASIC INDUSTRIES CORPORATION, Riyadh (SA)

(72) Inventors: Khalid Karim, Riyadh (SA); Abdulaziz Al Jodai, Riyadh (SA)

(73) Assignee: Saudi Basic Industries Corporation, Riyadh (SA)

( * ) Notice: Subject to any disclaimer, the term of this patent is extended or adjusted under 35 U.S.C. 154(b) by 0 days.

(21) Appl. No.: 14/785,992

(22) PCT Filed: Apr. 22, 2014

(86) PCT No.: PCT/IB2014/001432
§ 371 (c)(1),
(2) Date: Oct. 21, 2015

(87) PCT Pub. No.: WO2014/174375
PCT Pub. Date: Oct. 30, 2014

(65) Prior Publication Data
US 2016/0074841 A1    Mar. 17, 2016

Related U.S. Application Data

(60) Provisional application No. 61/815,418, filed on Apr. 24, 2013.

(51) Int. Cl.
*B01J 27/057* (2006.01)
*B01J 37/04* (2006.01)
(Continued)

(52) U.S. Cl.
CPC ....... *B01J 27/0576* (2013.01); *B01J 23/6527* (2013.01); *B01J 23/6562* (2013.01);
(Continued)

(58) Field of Classification Search
None
See application file for complete search history.

(56) References Cited

U.S. PATENT DOCUMENTS 3,098,102 A    7/1963   Bethell et al.
3,775,474 A   11/1973   Ohara et al.
(Continued)

FOREIGN PATENT DOCUMENTS

EP    1318127 A2    6/2003
EP    1521633 A1    4/2005
(Continued)

OTHER PUBLICATIONS

International Search Report mailed on Dec. 1, 2014 by the International Searching Authority for International Patent Application No. PCT/IB2014/001399, which was filed on Apr. 22, 2014 and published as WO 2014/174371 on Oct. 30, 2014 (Inventor—Karim et al; Applicant—Saudi Basic Industries Corp.; (5 pages).

(Continued)

*Primary Examiner* — Colin W Slifka
(74) *Attorney, Agent, or Firm* — Ballard Spahr LLP

(57) ABSTRACT

The present disclosures and inventions relate to composite catalyst compositions for the catalytic oxidation of hydrocarbons such as propane with an oxygen containing stream, in the presence of a composite catalyst comprising CA that comprises at least components a metal M, a support S, and an optional alkali metal A, and also CB that comprises one or more mixed metal oxide phases comprising metals in the relative molar ratios indicated by the formula $Mo_aV_bGa_cPd_dNb_eX_f$, to produce α,β-unsaturated carboxylic acids such as acrylic acid and/or olefins such as propylene.

19 Claims, 2 Drawing Sheets

(51) Int. Cl.
*B01J 37/08* (2006.01)
*C07C 51/215* (2006.01)
*C07C 5/03* (2006.01)
*B01J 23/652* (2006.01)
*B01J 23/656* (2006.01)
*B01J 23/68* (2006.01)
*B01J 23/89* (2006.01)
*B01J 35/02* (2006.01)
*B01J 23/88* (2006.01)
*B01J 23/887* (2006.01)

(52) U.S. Cl.
CPC ............ *B01J 23/686* (2013.01); *B01J 23/88* (2013.01); *B01J 23/8877* (2013.01); *B01J 23/8993* (2013.01); *B01J 35/023* (2013.01); *B01J 37/04* (2013.01); *B01J 37/08* (2013.01); *C07C 5/03* (2013.01); *C07C 51/215* (2013.01); *B01J 2523/00* (2013.01); *C07C 2527/057* (2013.01); *Y02P 20/582* (2015.11)

(56) References Cited

U.S. PATENT DOCUMENTS

| | | | |
|---|---|---|---|
| 4,035,262 | A | 7/1977 | Childress et al. |
| 6,114,278 | A | 9/2000 | Karim et al. |
| 6,160,162 | A | 12/2000 | Karim et al. |
| 6,646,158 | B1 | 11/2003 | Karim et al. |
| 6,906,208 | B2 | 6/2005 | Shan et al. |
| 7,285,514 | B2 | 10/2007 | Kang et al. |
| 2002/0115879 | A1 | 8/2002 | Hinago et al. |
| 2003/0088118 | A1 | 5/2003 | Komada et al. |
| 2003/0208085 | A1 | 11/2003 | Gaffney et al. |
| 2004/0030184 | A1 | 2/2004 | Cook et al. |
| 2005/0054869 | A1 | 3/2005 | Lugmair et al. |
| 2005/0131255 | A1* | 6/2005 | Benderly ............... B01J 23/002 562/546 |
| 2006/0047137 | A1 | 3/2006 | Tu et al. |
| 2006/0183941 | A1 | 8/2006 | Dubois et al. |
| 2006/0205978 | A1 | 9/2006 | Yunoki et al. |
| 2006/0235238 | A1 | 10/2006 | Komada et al. |
| 2006/0293538 | A1 | 12/2006 | Dubois et al. |
| 2007/0161767 | A1 | 7/2007 | Tu et al. |
| 2008/0139844 | A1 | 6/2008 | Dubois et al. |
| 2008/0194871 | A1 | 8/2008 | Dubois et al. |

FOREIGN PATENT DOCUMENTS

| | | | |
|---|---|---|---|
| EP | 1533029 | A1 | 5/2005 |
| EP | 1574254 | A2 | 9/2005 |
| EP | 1806178 | A1 | 7/2007 |
| JP | 2001-347165 | A | 12/2001 |
| JP | 2004-041839 | A | 2/2004 |
| JP | 2004-041880 | A | 2/2004 |
| JP | 2004-066024 | A | 3/2004 |
| JP | 2004-188341 | A | 7/2004 |
| JP | 2005-074377 | A | 3/2005 |
| WO | WO0029106 | * | 5/2000 |
| WO | WO-0029106 | A1 | 5/2000 |
| WO | WO-0183103 | A2 | 11/2001 |
| WO | WO-2004/007071 | | 1/2004 |
| WO | WO-2006/058998 | A2 | 6/2006 |
| WO | WO-2008/068332 | A1 | 6/2008 |
| WO | WO-2008/152952 | A1 | 12/2008 |

OTHER PUBLICATIONS

Guliants, V.V. et al., Mesoporous and Nanostructured Multicomponent Mo—V—Te—Nb—O Catalysts for Propane Ammoxidation to Acrylonitrile, AlChE Annual Meeting, Conference Proceedings (2006).

Herbet, R. et al., Nanostructured Vanadium Oxide Model Catalysts Based on Mesoporous SBA-15, Chemie-Ingenieur-Technik, 78(9): 1263 (2006) (Machine translation included).

Hess, C., Direct Correlation of the Dispersion and Structure in Vanadium Oxide Supported on Silica SBA-15, J Catalysis, 248(1): 120 (2007).

Hess, C., Nanostructured Vanadium Oxide Model Catalysts for Selective Oxidation Reactions, Chemphyschem, 10(2): 319 (2009).

International Search Report mailed on Jan. 29, 2015 by the International Searching Authority for International Patent Application No. PCT/IB2014/001432, which was filed on Apr. 22, 2014 and published as WO 2014/175375 (Inventor—Karim et al.; Applicant—Saudi Basic Industries Corp.; (5 pages).

* cited by examiner

US 9,636,663 B2

HIGH PRODUCTIVITY CATALYST FOR ALKANE OXIDATION TO UNSATURATED CARBOXYLIC ACIDS AND ALKENES

CROSS-REFERENCE TO RELATED APPLICATIONS

This is a U.S. National Phase Application of International Application No. PCT/IB2014/001432, filed Apr. 22, 2014, which claims the benefit of U.S. Provisional Application No. 61/815,418, filed on Apr. 24, 2013, which are both incorporated herein by reference in their entirety.

FIELD OF THE INVENTIONS

The present disclosures and inventions relate to composite catalyst compositions for the catalytic oxidation of alkanes, such as propane to unsaturated carboxylic acids and/or alkenes.

BACKGROUND

Conversion of alkanes, such as propane, to more valuable materials, such as unsaturated carboxylic acids and/or alkenes, for example, acrylic acid and propylene, is highly desired in industry. Propane and propylene are widely produced commercially from oil and natural gas via a variety of widely known processes in oil refineries. Propylene is useful for making a variety of additional downstream products via known commercial processes, and commands a significantly higher price than propane. The vapor phase oxidation of propylene to acrylic acid with air or oxygen, over supported catalysts is well-known in the art and widely commercially practiced.

Catalytic oxidation of propane to acrylic acid and propylene is economically attractive. For example, such approach is economically more attractive than one of production of acrylic acid via a process requiring propylene as a starting material, because of the significant price difference between propane and propylene as starting materials.

Accordingly, disclosed herein are catalytic compositions and methods related thereto useful in the oxidation of alkanes, such as propane, to unsaturated carboxylic acids and/or alkenes.

SUMMARY OF THE INVENTIONS

In accordance with the purpose(s) of the invention, as embodied and broadly described herein, this disclosure, in one aspect, relates to a composite catalyst composition comprising $C_A$ and $C_B$,
  a) wherein $C_A$ comprises at least components M and S, and optionally A,
    i) wherein M comprises at least one metal comprising B, La, Mn, Sb, Ti, Zr, Fe, Cs, Au, or Ce, or a mixture thereof;
    ii) wherein S is a support material, and
    iii) wherein A comprises an alkaline metal comprising Na, K, Mg, or Ca, or a mixture thereof; and
  b) wherein $C_B$ comprises one or more mixed metal oxide phases comprising metals in the relative molar ratios indicated by the formula $Mo_aV_bGa_cPd_dNb_eX_f$,
    i) wherein a is 1,
    ii) wherein b is from 0.01 to 0.9,
    iii) wherein c is greater than 0 to 0.2,
    iv) wherein d is from 0.0000001 to 0.2,
    v) wherein e is greater than 0 to 0.2,
    vi) wherein X comprises La, Te, Ge, Zn, Si, In, or W, or a mixture thereof, and
    vii) wherein f is greater than 0 to 0.5, and
  c) wherein $C_A$ is present in an amount of 1% by weight to 99% by weight and $C_B$ is present in an amount of 99% by weight to 1% by weight.

Also disclosed are methods of making the composite catalyst compositions described herein comprising the steps of
  a) mixing a support material S with a solution comprising one or more metal compounds comprising one or more metals M comprising B, La, Mn, Sb, Ti, Zr, Fe, Cs, Au, or Ce, or a mixture thereof, and optionally one or more alkali metal compounds comprising Na, K, Mg, or Ca or a mixture thereof, thereby dispersing the metal compounds and/or alkali metal compounds on the support material;
  b) calcining the support material dispersed with the metal and/or alkali metal compounds to form $C_A$;
  c) mixing $C_A$ with $C_B$, thereby forming the catalyst composition,
  d) wherein $C_B$ comprises one or more mixed metal oxide phases comprising metals in the relative molar ratios indicated by the formula $Mo_aV_bGa_cPd_dNb_eX_f$,
    i) wherein a is 1,
    ii) wherein b is from 0.01 to 0.9,
    iii) wherein c is greater than 0 to 0.2,
    iv) wherein d is from 0.0000001 to 0.2,
    v) wherein e is greater than 0 to 0.2,
    vi) wherein X comprises La, Te, Ge, Zn, Si, In, or W, or a mixture thereof, and
    vii) wherein f is greater than 0 to 0.5, and
  e) wherein $C_A$ is present in an amount of 1% by weight to 99% by weight and $C_B$ is present in an amount of 99% by weight to 1% by weight.

Also disclosed herein are methods of oxidizing a $C_2$-$C_{12}$ alkane comprising contacting a $C_2$-$C_{12}$ alkane with an oxygen containing stream and a composite catalyst composition comprising at least $C_A$ and $C_B$,
  a) wherein $C_A$ comprises at least components M and S, and optionally A,
    i) wherein M comprises at least one metal comprising B, La, Mn, Sb, Ti, Zr, Fe, Cs, Au, or Ce, or a mixture thereof;
    ii) wherein S is a support material, and
    iii) wherein A comprises an alkaline metal comprising Na, K, Mg, or Ca, or a mixture thereof; and
  b) wherein $C_B$ comprises one or more mixed metal oxide phases comprising metals in the relative molar ratios indicated by the formula $Mo_aV_bGa_cPd_dNb_eX_f$,
    i) wherein a is 1,
    ii) wherein b is from 0.01 to 0.9,
    iii) wherein c is greater than 0 to 0.2,
    iv) wherein d is from 0.0000001 to 0.2,
    v) wherein e is greater than 0 to 0.2,
    vi) wherein X comprises La, Te, Ge, Zn, Si, In, or W, or a mixture thereof, and
    vii) wherein f is greater than 0 to 0.5, and
  c) wherein $C_A$ is present in an amount of 1% by weight to 99% by weight and $C_B$ is present in an amount of 99% by weight to 1% by weight,
    thereby oxidizing the $C_2$-$C_{12}$ alkane.

It has been discovered that by combination of $C_A$ with $C_B$ as disclosed herein, to make a composite catalyst, the rate of hydrocarbon (such as alkanes, for example, propane) oxidation to form α,β-unsaturated carboxylic acids (such as acrylic acid) and olefins (such as propylene) can be increased.

Additional advantages will be set forth in part in the description which follows, and in part will be obvious from the description, or may be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

DESCRIPTION OF THE FIGURES

(FIG. 1A) and 305° C. (FIG. 1B), in a ratio compared to Experiment 14 results obtained from a "$C_B$," catalyst ($Mo_1V_{0.398}Ga_{1.0E-05}Pd_{1.90E04}Nb_{0.125}Te_{0.23}$) alone.

DETAILED DESCRIPTION

1. Definitions

Figure 1A:
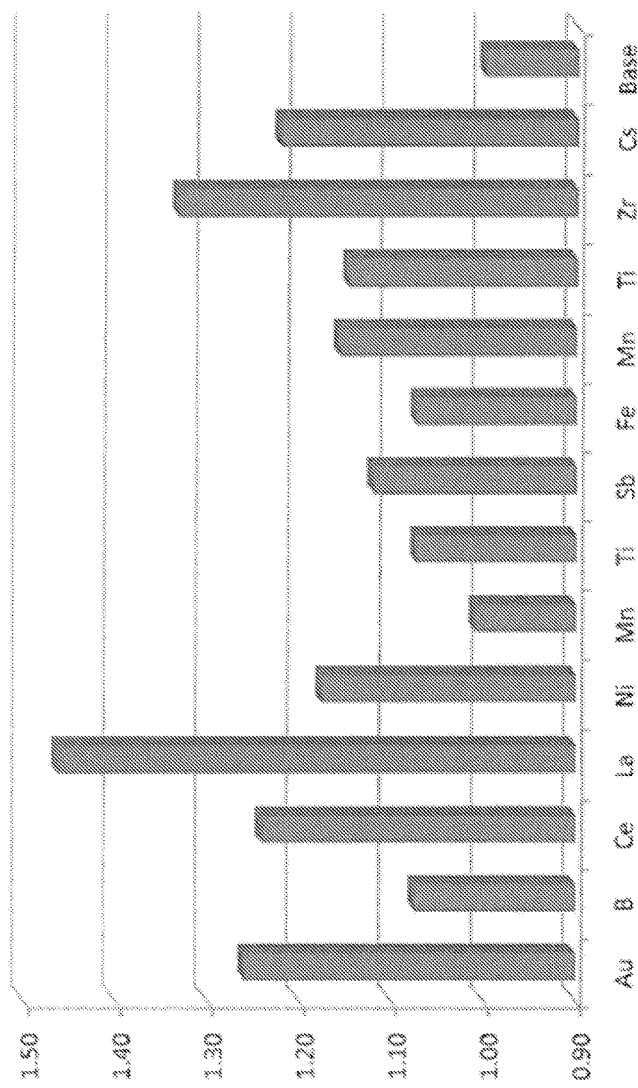
FIGS. 1A and 1B show bar charts of the rate data from Table 1, which describes the results of propane oxidation testing of each of the composite catalysts as described in Examples 1-13 at each of 290° C.

Disclosed herein are materials, compounds, compositions, and components that can be used for, can be used in conjunction with, can be used in preparation for, or are products of the disclosed methods and compositions. It is to be understood that when combinations, subsets, interactions, groups, etc. of these materials are disclosed, that while specific reference of each various individual and collective combination and permutation of these compounds may not be explicitly disclosed, each is specifically contemplated and described herein. For example, if a catalyst component is disclosed and discussed, and a number of alternative solid state forms of that component are discussed, each and every combination and permutation of the catalyst component and the solid state forms that are possible are specifically contemplated unless specifically indicated to the contrary. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denote the weight relationship between the element or component and any other elements or components in the composition or article for which a part by weight is expressed. Thus, in a compound containing 2 parts by weight of component X and 5 parts by weight of component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

Many of the catalyst compositions and/or catalyst components disclosed herein are described as containing a "metal" or "metals." Examples of such "metal" components include B, La, Mn, Sb, Ti, Zr, Fe, Cs, Au, and Ce, Na, K, Mg, or Ca, and La, Te, Ge, Zn, Si, In, or W. It should be understood that references to such "metals" in this application does NOT imply a particular valence, chemical, or physical state of those elements, or that those elements are necessarily in a zero valent state, or metallic solid physical state or alloy (although they could be in such states), but rather that the term "metal" or "metals" can also be present in a compound with other elements or groups wherein the metal can be present in any energetically feasible positive oxidation state (i.e. cationic oxidation states). For example, a reference to potassium (K) as a metal could include bulk metallic potassium in a zero oxidation state, or dispersions or solutions of potassium metal, or also the cationic form $K^+$ of potassium, which may be present in either liquid or crystalline solutions with other elements.

As used herein a "reference base catalyst" or the like terms refer to a catalyst with corresponding $C_B$ but without a $C_A$ corresponding to the disclosed composite catalyst composition herein. Thus, $C_A$ can be absent in a reference base catalyst. However, an incomplete $C_A$ could be present in a reference base catalyst. For example, a reference base catalyst can include $C_A$ but without M. Thus, for example, a reference base catalyst can be $C_B$ or $C_B$—S as described herein. A reference base catalyst is used under equivalent reaction conditions, i.e. oxidation conditions of propane, as the corresponding composite catalyst composition.

As used herein, the terms space time yield ("STY") refers to the tons or kg of product that is produced per unit time per volume of catalyst.

2. Composite Catalyst Compositions Useful for the Oxidation of Hydrocarbons

Disclosed herein are composite catalyst compositions useful for the oxidation of hydrocarbons, such as alkanes, for example, propane. The disclosed composite catalyst compositions can have a higher activity than a reference base catalyst. The disclosed composite catalyst compositions comprise $C_A$ and $C_B$, in which $C_A$ comprises a support S, one or more modifying metals M, and optionally one or more alkali metals A, and wherein $C_B$ is an active phase and comprises $Mo_aV_bGa_cPd_dNb_eX_f$. The active phase $C_B$ disclosed herein is at least partially described in PCT Publication WO 00/029106 and U.S. Pat. No. 6,160,162, which are both hereby incorporated by reference in their entirety, for their disclosure in general and for the specific disclosure of certain aspects of $C_B$.

Disclosed herein are composite catalyst compositions comprising $C_A$ and $C_B$,
a) wherein $C_A$ comprises at least components M and S, and optionally A,
  i) wherein M comprises at least one metal comprising B, La, Mn, Sb, Ti, Zr, Fe, Cs, Au, or Ce and a mixture thereof;
  ii) wherein S is a support material, and
  iii) wherein A comprises an alkaline metal comprising Na, K, Mg, or Ca, or a mixture thereof; and
b) wherein $C_B$ comprises one or more mixed metal oxide phases comprising metals in the relative molar ratios indicated by the formula $Mo_aV_bGa_cPd_dNb_eX_f$,
  i) wherein a is 1,
  ii) wherein b is from 0.01 to 0.9,
  iii) wherein c is greater than 0 to 0.2,
  iv) wherein d is from 0.0000001 to 0.2,
  v) wherein e is greater than 0 to 0.2,
  vi) wherein X comprises La, Te, Ge, Zn, Si, In, or W, and a mixture thereof, and
  vii) wherein f is greater than 0 to 0.5, and
wherein $C_A$ is present in an amount of 1% by weight to 99% by weight and $C_B$ is present in an amount of 99% by weight to 1% by weight.

The composite catalysts described herein are composite catalysts, in the sense that they comprise mixtures of at least $C_A$ and $C_B$.

In one aspect, $C_B$ can include any of the mixed metal oxide phases useful for air or oxygen oxidation of propane described in WO 00/029106 and U.S. Pat. No. 6,160,162. The $C_A$ comprises at least components M, S, and optionally A, and are intermixed with the $C_B$ to provide the composite catalysts.

Any relative proportion of the $C_A$ and $C_B$ phases can be present in the final composite catalysts. In one aspect, $C_A$ is present in an amount of 1% by weight to 99% by weight and $C_B$ is present in an amount of 99% by weight to 1% by weight. In another aspect, $C_A$ is present in an amount of 5% by weight to 90% by weight and $C_B$ is present in an amount of 95% by weight to 10% by weight. In yet another aspect, $C_A$ is present in an amount of 20% by weight to 40% by weight and $C_B$ is present in an amount of 80% by weight to 60% by weight. In yet another aspect, $C_A$ is present in an amount of 50% by weight to 90% by weight and $C_B$ is present in an amount of 50% by weight to 10% by weight. In yet another aspect, $C_A$ is present in an amount of 90% by weight and $C_B$ is present in an amount of 10% by weight. In yet another aspect, $C_A$ is present in an amount of 30% by weight and $C_B$ is present in an amount of 70% by weight.

a. $C_A$

The M component of $C_A$ comprises at least one metal (metal atoms or metal cations) comprising B (boron), La (lanthanum), Mn (manganese), Sb (antimony), Ti (titanium), Zr (zirconium), Fe (iron), Cs (cesium), Au (gold), or Ce (cerium), or a mixture thereof. In one aspect, M comprises La, Zr, Ce, or Cs, or a mixture thereof. In another aspect, M comprises La.

In one aspect, $C_A$ comprises at least 0.2% by weight of M. In another aspect, $C_A$ comprises at least 0.5% by weight of M. In yet another aspect, $C_A$ comprises at least 1% by weight of M. In yet another aspect, $C_A$ comprises at least 5% by weight of M. In yet another aspect, $C_A$ comprises at least 10% by weight of M. In yet another aspect, $C_A$ comprises at least 20% by weight of M. In yet another aspect, $C_A$ comprises at least 30% by weight of M. In yet another aspect, $C_A$ comprises at least 40% by weight of M. In yet another aspect, $C_A$ comprises at least 50% by weight of M.

In one aspect, $C_A$ comprises from 0.2% by weight to 70% by weight of M. In another aspect, $C_A$ comprises from 10% by weight to 60% by weight of M. In yet another aspect, $C_A$ comprises from 10% by weight to 30% by weight of M. In yet another aspect, $C_A$ comprises from 20% by weight to 60% by weight of M.

In one aspect, $C_A$ comprises at least 30% by weight of S. In another aspect, $C_A$ comprises at least 40% by weight of S. In yet another aspect, $C_A$ comprises at least 50% by weight of S. In yet another aspect, $C_A$ comprises at least 60% by weight of S. In yet another aspect, $C_A$ comprises at least 70% by weight of S. In yet another aspect, $C_A$ comprises at least 80% by weight of S. In yet another aspect, $C_A$ comprises at least 90% by weight of S. In yet another aspect, $C_A$ comprises at least 95% by weight of S. In yet another aspect, $C_A$ comprises at least 98% by weight of S.

In one aspect, $C_A$ comprises from 30% by weight to 98% by weight of S. In another aspect, $C_A$ comprises from 40% by weight to 98% by weight of S. In yet another aspect, $C_A$ comprises from 50% by weight to 95% by weight of S.

The A component of the $C_A$ can be optionally present, and can comprise alkali metals, such as Na (sodium), K (potassium), Mg (magnesium) or Ca (calcium), or a mixture thereof. In one aspect, A comprises K, Na, or a mixture thereof.

In one aspect, A is present. In another aspect, A is absent. In one aspect, $C_A$ comprises at least 1% by weight of A. In another aspect, $C_A$ comprises at least 3% by weight of A. In yet another aspect, $C_A$ comprises at least 5% by weight of A. In yet another aspect, $C_A$ comprises at least 10% by weight of A. In yet another aspect, $C_A$ comprises at least 15% by weight of A. In yet another aspect, $C_A$ comprises at least 20% by weight of A. In yet another aspect, $C_A$ comprises at least 25% by weight of A. In yet another aspect, $C_A$ comprises at least 30% by weight of A. In yet another aspect, $C_A$ comprises at least 40% by weight of A.

In one aspect, $C_A$ comprises from 1% by weight to 40% by weight of A. In another aspect, $C_A$ comprises from 1% by weight to 20% by weight of A. In yet another aspect, $C_A$ comprises from 5% by weight to 15% by weight of A.

The S support material of the $C_A$ can be any of the inorganic solid materials well known to those of ordinary skill in the art that are known to be usably stable in the presence of oxygen gas at the high temperatures of propane oxidation reactions (up to 600° C., or in some aspects up to between 150° C. and 450° C.). In one aspect, the support materials comprises many metal oxides, clays, silicates, aluminosilicates, aluminas, metal phosphates, metal carbides or metal nitrides, zeolites, molecular sieves, etc. In another aspect, S comprises $Al_2O_3$, $SiO_2$, $TiO_2$, $CeO_2$, $AlPO_4$, $ZrO_2$, SiC, Mo-carbide, aluminumsilicate, zeolites, or molecular sieves, or a mixture thereof. In yet another aspect, S comprises $Al_2O_3$ (alumina in its various forms) or $SiO_2$ (silica) or a mixture thereof. In yet another aspect, S comprises $\alpha$-$Al_2O_3$. These support materials can be either high or low surface area, and porous or non-porous, micro-porous, or meso-porous. In one aspect, the support material is micro-porous, or meso-porous.

The M and/or A components can be dispersed into and/or over the support material S. In some embodiments, M and/or A are nano-dispersed into or over the support S. Nano-dispersed refers to metal particles having a size in the nanometer (i.e. from 1 nm to 1000 nm) range which are dispersed over a larger surface area (i.e. >1 micron to 1000 microns). In one aspect, the metal particles can be dispersed so that any deep oxidation reactions are prevented.

b. $C_B$

The $C_B$ used as a component of the composite catalyst compositions of the inventions can comprise any of the mixed metal oxide compositions disclosed herein and is at least partially described in WO 00/029106 and U.S. Pat. No. 6,160,162. The solid mixed metal oxides are themselves (alone) active for the oxidation of hydrocarbons such as propane, and comprise a mixture of several metals in molar ratios as described by the formula:

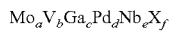

$$Mo_a V_b Ga_c Pd_d Nb_e X_f$$

wherein a is 1, wherein b is from 0.01 to 0.9, wherein c is greater than 0 to 0.2, wherein d is from 0.0000001 to 0.2, wherein e is greater than 0 to 0.2, wherein X comprises La, Te, Ge, Zn, Si, In, or W, or a mixture thereof, and wherein f is greater than 0 to 0.5. In one aspect of those mixed metal oxides, X comprises Te (tellurium) or is Te. In one aspect, b is from 0.1 to 0.9. In another aspect, b is from 0.1 to 0.5. In one aspect, c is greater than 0 to 0.001. In another one aspect, c is greater than 0 to 0.0001. In one aspect, d is from 0.0000001 to 0.01. In another aspect, d is from 0.00001 to 0.01. In one aspect, e is from 0.05 to 0.2. In another aspect, e is from 0.1 to 0.2. In one aspect, f is from 0.05 to 0.5. In another aspect, f is from 0.1 to 0.5. In one aspect, a is 1, wherein b is from 0.1 to 0.5, c is greater than 0 to 0.0001, d is from 0.00001 to 0.01, e is from 0.1 to 0.2, X is Te, and wherein f is from 0.1 to 0.5.

In one aspect, $C_B$ can comprise the formula $Mo_1 V_{0.398} Ga_{1.0E-05} Pd_{1.90E-04} Nb_{0.125} X_f$. In another aspect, $C_B$ can comprise the formula $Mo_1 V_{0.398} Ga_{1.0E-05} Pd_{1.90E-04} Nb_{0.125} Te_{0.23}$. In another aspect, $C_B$ can comprise the formula $Mo_1 V_{0.398} Ga_{1.0E-05} Pd_{1.90E-04} Nb_{0.125} Te_{0.23} Zn_{1.0E-05}$.

It should be understood that the mixed oxides used for the $C_B$ of the disclosed mixed metal oxides, wherein the metal atoms or ions are present in the spaces between a solid lattice formed by oxide anions, which could be represented by the formula

$$Mo_a V_b Ga_c Pd_d Nb_e X_f O_g$$

wherein a, b, c, d, e, and f have the same meanings as above, and g can be a broad numerical range representing the number of oxygen atoms in the mixed metal oxide composition, that is determined stoichiometrically.

It is to be recognized that the mixed metal oxides in the disclosed compositions can be single phase solid materials whose composition cannot be represented by simple ratios of well-defined integers, because those solids probably contain solid state point defects (such as vacancies or interstitial atoms or ions) that can cause variations in the overall stoichiometry of the composition, a phenomenon well known to those of ordinary skill in the arts related to solid inorganic materials, especially for transition metal oxides. Accordingly, for convenience and the purposes of this disclosure, the stoichiometric composition of the catalytically active mixed metal oxides described herein are quoted in ratios of moles of the other atoms as compared to the moles of molybdenum ions or atoms in the same composition (i.e. a=1).

It should also be recognized that the $C_B$ component composition can itself be disposed and/or dispersed on a same or different support material, including those described above for the $C_A$. Suitable supports for the $C_B$ component of the catalyst include alumina, silica, titania, zirconia, zeolites, silicon carbide, Mo carbide, molecular sieves and other micro/nonporous materials, and a mixture thereof.

The composite catalyst composition, once formed, is typically ground to provide catalyst particles of a size sufficient to have physical integrity, but small enough to allow diffusion of reactants and products to the catalyst surfaces. In one aspect, the catalyst composition has a particle size from 20 μm to 500 μm.

In one aspect, the composite catalyst composition is stable to at least 600° C. Accordingly, no leaching, boiling, or sublimation of the metals in the catalyst occurs at such temperatures.

3. Methods for Preparing the Composite Catalyst Compositions

The disclosed composite catalyst compositions can be prepared by many methods and their variations that would be obvious to those of ordinary skill in the art, including the methods explicitly described herein below.

Also disclosed herein are methods of making the composite catalyst compositions disclosed herein.

In one aspect, the inventions described herein comprise the steps of:
a) mixing a support material S with a solution comprising one or more metal compounds comprising one or more metals M comprising B, La, Mn, Sb, Ti, Zr, Fe, Cs, Au, or Ce, or a mixture thereof, and optionally one or more alkali metal compounds comprising Na, K, Mg, or Ca or a mixture thereof, thereby dispersing the metal compounds and/or alkali metal compounds on the support material;
b) calcining the support material dispersed with the metal and/or alkali metal compounds to form $C_A$;
c) mixing $C_A$ with $C_B$, thereby forming the catalyst composition,
d) wherein $C_B$ comprises one or more mixed metal oxide phases comprising metals in the relative molar ratios indicated by the formula $Mo_a V_b Ga_c Pd_d Nb_e X_f$
   i) wherein a is 1,
   ii) wherein b is from 0.01 to 0.9,
   iii) wherein c is greater than 0 to 0.2,
   iv) wherein d is from 0.0000001 to 0.2,
   v) wherein e is greater than 0 to 0.2,
   vi) wherein X comprises La, Te, Ge, Zn, Si, In, or W, or a mixture thereof, and
   vii) wherein f is greater than 0 to 0.5, and
wherein $C_A$ is present in an amount of 1% by weight to 99% by weight and $C_B$ is present in an amount of 99% by weight to 1% by weight.

It should be understood that the descriptions of the various catalyst components and relevant numerical ratios described above in connection with the composite catalysts themselves can be and/or are applicable in connection with the methods for making those catalysts.

The first step of the methods described above provide for mixing a support material S with a solution (or liquid slurry or suspension) comprising one or more metal compounds comprising one or more metals M comprising B, La, Mn, Sb, Ti, Zr, Fe, Cs, Au, or Ce, or a mixture thereof, and optionally one or more alkali metal compounds comprising Na, K, Mg, or Ca, or a mixture thereof. The mixing disperses the metal compounds and/or alkali metal compounds on the support material. Many metal compounds or salts are suitable sources of the metals M and/or alkali metals used to make the $C_A$ composition.

There are many potential forms and formulas for compounds that could be used as a source of the various metals employed, including M, A, and X, or the metals used in the preparation of the $C_B$ metal oxide. Both inorganic salts (such as halides, nitrates, hydroxides, oxides, and the like) could be employed, or organic salts of the metals with alkoxides, carboxylic acids, amines or ammonium salts, organic chelating ligands, and the like can all be employed as sources of the M, A, and X metals.

In the second step of the process for making the composite catalysts, the support material that has been dispersed with the M metal compounds and/or A alkali metal compound used to make the $C_A$ is calcined, thereby, in one aspect forming the catalyst form $C_A$. Calcining is typically performed by initially baking or heating the $C_A$ at temperatures just above the boiling point of water, then further heating the catalysts in air at much higher temperatures, up to 450° C., or up to 600° C., for several hours.

The $C_B$ can be prepared by the similar methods disclosed in WO 00/029106 and U.S. Pat. No. 6,160,162. In one aspect, molybdenum is introduced into a solution in the form of ammonium salts such as ammonium paramolybdate, or as organic acid salts of molybdenum such as acetates, oxalates, mandelates, and glycolates. Other partially water soluble molybdenum compounds which can be used include molybdenum oxides, molybdic acid, and chlorides of molybdenum. In one aspect, vanadium is introduced into the solution in the form of ammonium salts such as ammonium metavanadate and ammonium decavanadate, or as organic salts of vanadium such as acetates, oxalates, and tartrates. Partially water soluble vanadium compounds such as vanadium oxides, and sulfates of vanadium can also be used. To achieve complete solubility, a certain amount of oxalic or tartaric acid can be added. In one aspect, gallium is introduced into the catalyst solution or slurry in the form of salts of gallium such as oxide, chloride, nitrate, and the like. In one aspect, palladium is introduced into the catalyst slurry in the form of Pd on activated charcoal or alumina or as a solution of salts of palladium such as acetates, chlorides, nitrates, and the like. In one aspect, niobium is used in the form of oxalates or hydrate oxides. Other sources of this metal in soluble form include compounds in which the metal is coordinated, bonded or complexed to a beta-diketonate, carboxylic acid, an amine, an alcohol, or an alkanolamine.

In one aspect of the mixed metal oxides of the $C_B$, catalysts comprising both Mo and V are prepared by the following general procedure. Aqueous solutions of vanadium and molybdenum are prepared separately. The vanadium solution is mixed with the molybdenum solution at a specified temperature and pH. The remaining required components are slowly added to the combined gel solution. After mixing, the resultant gel is dried to incipient wetness with continuous stirring. After initially drying the resultant gel mixture (for example at 120° C. for 16 hours), the resultant solid catalyst is heated to 350° C. and calcined at this temperature in air (for example for 4 hours) to produce the desired mixed metal oxide composition.

It should also be recognized that many potential solvents and many potential organic additives could be used to form the requisite solutions, slurries, or suspensions. In many embodiments water, possibly in combination with a variety of polar organic solvents, acids, or bases, or a mixture thereof could be used to form the requisite solutions, slurries, or solutions.

Once the $C_A$ and $C_B$ have been separately formed, they are mixed to form the composite catalyst composition, in ratios described above.

In one aspect of the methods of making the composite catalysts, the support material is dried prior to being mixed with the metal. Furthermore, in many embodiments, the steps of the method include further baking the composite catalyst composition.

After the composite catalyst composition has been formed from $C_A$ and $C_B$, it is often physically modified by various methods well known in the art, into particles having a size from 20 μm to 1000 μm. In one aspect, the composite catalyst composition has a size from 20 μm to 500 μm.

4. Methods for Oxidizing Alkanes with an Oxygen Containing Stream With a Composite Catalyst Composition Comprising at Least $C_A$ and $C_B$ Also disclosed herein are methods of oxidizing a $C_2$-$C_{12}$ alkane comprising contacting a $C_2$-$C_{12}$ alkane with an oxygen containing stream and a composite catalyst composition comprising at least $C_A$ and $C_B$, a) wherein $C_A$ comprises at least components M and S, and optionally A,
  i) wherein M comprises at least one metal comprising B, La, Mn, Sb, Ti, Zr, Fe, Cs, Au, or Ce, or a mixture thereof;
  ii) wherein S is a support material, and
  iii) wherein A comprises an alkaline metal comprising Na, K, Mg, or Ca, or a mixture thereof; and
b) wherein $C_B$ comprises one or more mixed metal oxide phases comprising metals in the relative molar ratios indicated by the formula $Mo_aV_bGa_cPd_dNb_eX_f$,
  i) wherein a is 1,
  ii) wherein b is from 0.01 to 0.9,
  iii) wherein c is greater than 0 to 0.2,
  iv) wherein d is from 0.0000001 to 0.2,
  v) wherein e is greater than 0 to 0.2,
  vi) wherein X comprises La, Te, Ge, Zn, Si, In, or W, or a mixture thereof, and
  vii) wherein f is greater than 0 to 0.5, and
c) wherein $C_A$ is present in an amount of 1% by weight to 99% by weight and $C_B$ is present in an amount of 99% by weight to 1% by weight,
thereby oxidizing the $C_2$-$C_{12}$ alkane.

It has been discovered that by inclusion of a $C_A$ catalyst with a $C_B$ catalyst, to make a composite catalyst as has been described above, the rate of hydrocarbon oxidation to form α,β-unsaturated carboxylic acids (such as acrylic acid) and olefins (such as propylene) can be increased.

It should be understood that the descriptions of the various catalyst components and relevant numerical ratios described above in connection with the composite catalysts themselves can be and/or are applicable in connection with the methods of oxidizing alkanes described here.

The catalytic methods described here relate to methods for the catalytic oxidation of $C_2$-$C_{12}$ alkanes with an oxygen containing stream in the presence of a composite catalyst as described above. Any $C_2$-$C_{12}$ alkane that can be vaporized and mixed with an oxygen containing stream in a non-explosive composition (which may contain a carrier gas diluent) can be used in the method, to produce the corresponding olefins (comprising carbon-carbon double bonds, especially propylene, or α,β-unsaturated carboxylic acids, such as acrylic acid. Examples of suitable alkanes include ethane, propane, and various isomers of $C_4$-$C_{12}$ alkanes such as butanes, pentanes, hexanes, heptanes, octanes, nonanes, decanes, unadecanes, and dodecanes. In one aspect, the $C_2$-$C_{12}$ alkanes comprise propane. In another aspect, the $C_2$-$C_{12}$ alkanes comprise $C_2$-$C_6$ alkanes. In yet another aspect, the $C_2$-$C_{12}$ alkanes comprise $C_2$-$C_4$ alkanes. In one aspect, propane is employed in the method, in order to produce desirable products like acrylic acid and/or propylene.

In one aspect of the method, oxidation of a $C_2$-$C_{12}$ alkane produces a product molecule comprising a carboxylic acid, or a product molecule comprising a carbon-carbon double bond. In one aspect of the method, the oxidation produces a molecule comprising a carboxylic acid and a carbon-carbon double bond.

The composite catalysts used in the methods comprise both $C_A$ and $C_B$, as already described above, and the various components of those composite catalysts already described above.

The catalytic methods of the invention typically pass feed stream comprising a mixture of a vaporized alkane such as propylene, oxygen gas or air, or air supplemented with additional oxygen, and an optional carrier gas, and contact that feed stream with the composite catalyst at a suitable elevated temperature and pressure, by flowing the vapor feed stream into and over the catalyst.

The catalyst can be contained within any suitable reactor vessel, in a fixed bed, fluidized bed, or any of the many other arrangements known to those of ordinary skill in the catalytic arts.

The feed stream used as the source of the alkane (especially propane) can be a gas stream which contains at least three volume percent of the alkanes (often propane or a mixture of propylene/propane), and often contains less than thirty volume percent of alkane. The gas stream can also contain major amounts, more than five volume percent, of diluents such as nitrogen/argon, carbon dioxide, and water in the form of steam. In many embodiments, the reaction mixture generally contains, per one mole of propane, from 0.01 to 2.0 moles of molecular oxygen, either as pure oxygen or in the form of air, and from zero to 4.0 moles of water in the form of steam. The ratio of propane to oxygen varies with the desired conversion of propane and the selectivity of the catalyst, but generally is in the range of 1/5-5/1. The ratio of propane to diluents can be in the range of 1/5-1/1. Other gases may be used as reaction diluents or heat moderators such as helium, nitrogen and carbon dioxide.

Suitable temperatures for the contacting step often occur between 150° C. and 450° C., or between 280° C. and 310° C. Suitable pressures for the contacting step often occur at a pressure from 1 to 50 bar. The reaction pressure can be initially provided by the feed of the gaseous reactant and diluent and after the reaction has commenced, can be maintained by the use of a suitable back-pressure controller placed on the reactor outlet stream. The liquid products of the reaction can be separated from the unreacted feed hydrocarbons by condensation or scrubbing, and usually by water or dilute acid in the case of carboxylic acids such as acrylic acid.

The contacting of the feed stream with the composite catalyst is typically carried out with a contact time between the feed stream and the catalyst from 0.01 second to 100 seconds, or from 0.1 second to 10 seconds; the contact time is defined as the ratio between the apparent volume of the catalyst bed and the volume of the gaseous reaction mixture feed to the catalyst bed under the given reaction conditions in a unit of time.

The contacting of the feed stream with the composite catalyst is typically carried out at a space hourly velocity from 50 to 50,000 $hr^{-1}$, or from 100 to 10,000 $hr^{-1}$ or from 200 to 3,000 $hr^{-1}$. The space velocity is calculated by determining the total reactor outlet gas equivalent in liters of the total effluent evolved over a period of one hour divided by the liters of catalyst in the reactor. This room temperature volume is converted to the volume at 0° C. at 1 bar.

One advantage of the catalyst systems of the invention is the high yields of acrylic acid production achieved. The oxidation can provide at least a 30% yield, or a 50% yield, or a 70% yield of acrylic acid. In one aspect, less than 1% propylene is formed using the composite catalyst and methods of the invention.

In one aspect, the selectivity of conversion to acrylic acid is at least 50% per single pass through the composite catalyst composition. In another aspect, no detectable propylene is formed as a by-product.

One benefit of using the disclosed composite catalyst compositions are high rates of oxidation of alkanes. In one aspect, the space time yield (STY) for oxidation of propane to acrylic acid plus propylene is at least 20% higher relative to a base reference catalyst. In some related embodiments the STY for oxidation of propane to acrylic acid plus propylene is at least 30% higher relative to a base reference catalyst. In other related embodiments, the STY for oxidation of propane to acrylic acid plus propylene is at least 40% higher relative to a reference base catalyst.

The process is generally carried out in a single stage with all the oxygen and reactants being supplied as a single feed with non-reacted initial reactants being recycled. However, multiple stage addition of oxygen or hydrocarbon to the reactor can be used and/or recycling of un-reacted gases with purge mode can be applied to improve the overall productivity and/or yield of the desired products.

5. Aspects of the disclosed compositions and methods

Aspect 1: A composite catalyst composition comprising $C_A$ and $C_B$,
  a) wherein $C_A$ comprises at least components M and S, and optionally A,
    i) wherein M is at least one metal comprising B, La, Mn, Sb, Ti, Zr, Fe, Cs, Au, or Ce, or a mixture thereof;
    ii) wherein S is a support material, and
    iii) wherein A is an alkaline comprising Na, K, Mg, or Ca, or a mixture thereof; and
  b) wherein $C_B$ comprises one or more mixed metal oxide phases comprising metals in the relative molar ratios indicated by the formula $Mo_aV_bGa_cPd_dNb_eX_f$,
    i) wherein a is 1,
    ii) wherein b is from 0.01 to 0.9,
    iii) wherein c is greater than 0 to 0.2,
    iv) wherein d is from 0.0000001 to 0.2,
    v) wherein e is greater than 0 to 0.2,
    vi) wherein X comprises La, Te, Ge, Zn, Si, In, or W, or a mixture thereof, and vii) wherein f is greater than 0 to 0.5, and
  c) wherein $C_A$ is present in an amount of 1% by weight to 99% by weight and $C_B$ is present in an amount of 99% by weight to 1% by weight.

Aspect 2: The catalyst composition of aspect 1, wherein A is present.

Aspect 3: The catalyst composition of aspect 1 or 2, wherein A is present and comprises K or Na.

Aspect 4: The catalyst composition of any one of aspects 1-3, wherein $C_A$ is present in an amount from 20% by weight to 40% by weight and $C_B$ is present in an amount from 80% by weight to 60% by weight.

Aspect 5: The catalyst composition of any one of aspects 1-4, wherein S comprises $Al_2O_3$, $SiO_2$, $TiO_2$, $CeO_2$, $AlPO_4$, ZrO$_2$, SiC, Mo-carbide, aluminumsilicate, a zeolite, or a molecular sieve, or a mixture thereof.

Aspect 6: The catalyst composition of any one of aspects 1-5, wherein S comprises Al$_2$O$_3$ or SiO$_2$.

Aspect 7: The catalyst composition of any one of aspects 1-6, wherein M is dispersed over S.

Aspect 8: The catalyst composition of any one of aspects 1-7, wherein M is nano-dispersed over S.

Aspect 9: The catalyst composition of any one of aspects 1-8, wherein S is a microporous or mesoporous material.

Aspect 10: The catalyst composition of any one of aspects 1-9, wherein the catalyst composition has a particle size from 20 μm to 500 μm.

Aspect 11: The catalyst composition of any one of aspects 1-10, wherein M comprises La, Zr, Ce, or Cs, or a mixture thereof.

Aspect 12: The catalyst composition of any one of aspects 1-11, wherein M comprises La.

Aspect 13: The catalyst composition of any one of aspects 1-12, wherein X comprises Te.

Aspect 14: The catalyst composition of any one of aspects 1-13, wherein the catalyst composition is stable to at least 600° C.

Aspect 15: The catalyst composition of aspect 1, wherein the catalyst composition $C_A$ is present in an amount from 20% by weight to 40% by weight and $C_B$ is present in an amount from 80% by weight to 60% by weight, wherein A is present, wherein S comprises Al$_2$O$_3$ or SiO$_2$ wherein M comprises La, and wherein X comprises Te.

Aspect 16: A method of oxidizing a $C_2$-$C_{12}$ alkane comprising contacting a $C_2$-$C_{12}$ alkane with an oxygen containing stream and the composite catalyst composition of any one of aspects 1-15, thereby oxidizing the $C_2$-$C_{12}$ alkane.

Aspect 17: The method of aspect 16, wherein contacting occurs between 150° C. and 450° C.

Aspect 18: The method of aspect 16 or 17, wherein contacting occurs between 280° C. and 310° C.

Aspect 19: The method of any one of aspects 16-18, wherein contacting occurs at a pressure from 1 to 50 bar.

Aspect 20: The method of any one of aspects 16-19, wherein contacting occurs in the presence of a diluent gas.

Aspect 21: The method of any one of aspects 16-20, wherein contacting occurs at an hourly space velocity from 50 to 50,000 h$^{-1}$.

Aspect 22: The method of any one of aspects 16-21, wherein the $C_2$-$C_{12}$ alkane comprises propane.

Aspect 23: The method of any one of aspects 16-22, wherein the oxidation produces a composition comprising acrylic acid.

Aspect 24: The method of any one of aspects 16-23, wherein the selectivity of conversion to acrylic acid is at least 50% per single pass through the composite catalyst composition.

Aspect 25: The method of any one of aspects 16-22, wherein the oxidation produces a composition comprising a $C_2$-$C_{12}$ alkene.

Aspect 26: The method of any one of aspects 16-22, wherein the oxidation produces a composition comprising propylene.

Aspect 27: The method of any one of aspects 16-22, wherein the oxidation produces a composition comprising acrylic acid and propylene.

Aspect 28: The method of any one of aspects 16-22, wherein the oxidation produces a molecule comprising a carboxylic acid moiety.

Aspect 29: The method of any one of aspects 16-22, wherein the oxidation produces a molecule comprising a carbon-carbon double bond.

Aspect 30: The method of any one of aspects 16-22, wherein the oxidation produces a molecule comprising a carboxylic acid moiety and a carbon-carbon double bond.

Aspect 31: The method of aspect 27, wherein the space time yield (STY) for oxidation of propane to acrylic acid plus propylene is at least 20% higher relative to a reference base catalyst.

Aspect 32: The method of aspect 27, wherein the STY for oxidation of propane to acrylic acid plus propylene is at least 30% higher relative to a reference base catalyst.

Aspect 33: The method of aspect 27, wherein the STY for oxidation of propane to acrylic acid plus propylene is at least 40% higher relative to a reference base catalyst.

Aspect 34: A method of making a composite catalyst composition comprising the steps of
a) mixing a support material S with a solution comprising one or more metal compounds comprising one or more metals M comprising B, La, Mn, Sb, Ti, Zr, Fe, Cs, Au, or Ce, or a mixture thereof, and optionally one or more alkali metal compounds comprising Na, K, Mg, or Ca, or a mixture thereof, thereby dispersing the metal compounds and/or alkali metal compounds on the support material; and
b) calcining the support material dispersed with the metal and/or alkali metal compounds to form $C_A$;
c) mixing $C_A$ with $C_B$, thereby forming the catalyst composition,
  i) wherein $C_B$ comprises one or more mixed metal oxide phases comprising metals in the relative molar ratios indicated by the formula Mo$_a$V$_b$Ga$_c$Pd$_d$Nb$_e$X$_f$,
    (1) wherein a is 1,
    (2) wherein b is from 0.01 to 0.9,
    (3) wherein c is greater than 0 to 0.2,
    (4) wherein d is from 0.0000001 to 0.2,
    (5) wherein e is greater than 0 to 0.2,
    (6) wherein X comprises La, Te, Ge, Zn, Si, In, or W, or a mixture thereof, and
    (7) wherein f is greater than 0 to 0.5, and
  ii) wherein $C_A$ is present in an amount of 1% by weight to 99% by weight and $C_B$ is present in an amount of 99% by weight to 1% by weight.

Aspect 35: The method of aspect 34, wherein the support material is dried prior to being mixed with the metal.

Aspect 36: The method of aspect 34 or 35, wherein the method further comprises baking the catalyst composition.

Aspect 37: The method of any one of aspects 34-36, wherein the method further comprises physically modifying the catalyst composition into particles having a size from 20 μm to 500 μm.

EXAMPLES

The following examples are put forth so as to provide those of ordinary skill in the art with a complete disclosure and description of how the compounds, compositions, articles, devices, and/or methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

1. Standard Procedure for Propane Oxidation Catalyst Testing Experiments

All the specific catalysts described in these Examples were tested for catalyst activity for propane oxidation using a standard procedure described here. Catalyst evaluations were carried out using 0.10-0.40 gram of 38-425 mesh size catalyst samples placed into a stainless steel fixed bed tubular reactor and fed a mixture containing propane:oxygen:nitrogen at a ratio of 71.25:23.75:5 (at a temperature of 290-305° C., pressure of 15 psi and at space velocity of 1,090 h$^{-1}$).

Reaction products were analyzed on-line by gas chromatography. Oxygen, argon and carbon monoxide were analyzed using a 2.5 mm by 3 mm column of 13.times.molecular sieve. Carbon dioxide, propane and propylene were analyzed using a 2 mm by 3 mm column packed with material sold under the trade name HAYESEP Q®. Liquids products (acrylic acid, acrolein, acetic acid and water) were collected for a certain period in the cold trap and were analyzed using a 2 mm by 3 mm column packed with material sold under the tradename PORAPAK Q® In all cases, the conversion and selectivity calculations were based on reaction stoichiometry.

2. Example $C_B$: Preparation of an Exemplary $C_B$ Catalyst Component (Corresponds to Example 14 in Table 1): $Mo_1V_{0.398}Ga_{1.0E-05}Pd_{1.90E-04}Nb_{0.125}Te_{0.23}$ An example of the $C_B$ catalyst materials as disclosed herein having the composition cited above was prepared by methods described in U.S. Pat. No. 6,160,162. Ammonium metavanadate (Aldrich Chemicals, Assay=99.0%) in the amount of 7.6 grams was added to 80 ml of distilled water and heated to 90° C. with stirring. 3.4 grams of niobium oxide (80% $Nb_2O_5$), 28 grams of oxalic acid, and 28.8 g ammonium paramolybdate tetra hydrate (Aldrich Chemicals A.C.S.-12054-85-2) were added to the vanadate solution to make a gel mixture. The required amount of palladium followed by telluric acid and gallium oxide was added slowly to the gel mixture. The gel mixture was stirred vigorously to achieve a homogeneous gel mixture which was then dried slowly to incipient dryness with continuous stirring. The resulting solid was put in a China dish and dried additionally in an oven at 120° C. The dried material was cooled to room temperature and placed in a furnace where the catalyst was calcined at 300 to 600° C. for 4 to 16 hours.

The reaction product showed the following results: Propane Conversion (%):12; Acrylic acid sel. (%):60; Propylene sel. (%):10; Acetic acid sel. (%):10; COx sel. (%):20. The overall reaction products showed 80% of partial oxidation product and 20% $CO_x$.

3. Example 1—Preparation of $Mo_1V_{0.398}Ga_{1.0E-05}Pd_{1.90E-04}Nb_{0.125}Te_{0.23}$—$AuAl_2O_3$ α-$Al_2O_3$ was dried overnight at 110-120° C. (5° C./min heating rate). A solution of Au precursors was prepared by dissolving 0.2498 g $HAuCl_4$ in water in a 5 ml volumetric flask. The concentration of the solution was 0.05 g/ml on a metal only basis. To 0.100 g of the α-$Al_2O_3$ was added to 83 µl of the Au stock solution and 417 µl water. The excess liquids were slowly removed for 8-16 hours at 110-120° C. (heating rate 5° C./min) After drying at 120° C. the modified α-$Al_2O_3$ was calcined in air at 300-500° C. for 4-10 hours (5° C./min heating rate). The calcined material was finally crushed to a fine powder. 0.45 g α-$Al_2O_3$, then 50 mg of the finely ground active phase ($Mo_1V_{0.398}Ga_{1.0E-05}Pd_{1.90E04}Nb_{0.125}Te_{0.23}$) was mixed with 500 µL water and placed in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns. The catalyst thus prepared was tested under standard reaction conditions for propane oxidation as described above. Results are listed in Table 1.

4. Example 2—Preparation of $Mo_1V_{0.398}Ga_{1.0E-05}Pd_{1.90E-04}Nb_{0.125}Te_{0.23}$—$BaAl_2O_3$ α-$Al_2O_3$ was dried overnight at 110-120° C. (5° C./min heating rate). A solution of the Boron precursor was prepared by dissolving 0.5015 g $H_3BO_4$ in water using a 10 ml volumetric flask. The concentration of the solution was 0.05 g/mL on a metal salt basis. To 0.100 g of the α-$Al_2O_3$ was added 201 µl of the Boron stock solution and 299 µl water. The excess liquids were slowly removed for 8-16 hours at 110-120° C. (heating rate 5° C./min) After drying at 120° C. the modified α-$Al_2O_3$ was calcined in air at 300-500° C. for 4-10 hours (5° C./min heating rate). The calcined material was finally crushed to a fine powder. 0.45 g α-$Al_2O_3$ and 50 mg of the finely grinded active phase ($Mo_1V_{0.398}Ga_{1.0E-05}Pd_{1.90E-04}Nb_{0.125}Te_{0.23}$) was mixed with 500 µL water and placed in a small metal holder. Two small steel balls were used to grind the mixture in order to get an homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns and tested under standard reaction conditions for propane oxidation.

5. Example 3—Preparation of $Mo_1V_{0.398}Ga_{1.0E-05}Pd_{1.90E-04}Nb_{0.125}Te_{0.23}$—$CeAl_2O_3$ α-$Al_2O_3$ was dried overnight at 110-120° C. (5° C./min heating rate). A stock solution of the Ce precursors was prepared by dissolving 0.2554 g $Ce(NO_3)_3$ $6H_2O$ in water using a 5.000 ml volumetric flask. The concentration of the solutions was 0.05 g/mL on a metal salt basis. To 0.100 g of the α-$Al_2O_3$ was added 124 µl of the Ce stock solution and 376 µl water. The excess liquids were slowly removed for 8-16 hours at 110-120° C. (heating rate 5° C./min) After drying at 120° C. the modified α-$Al_2O_3$ were calcined in air at 300-500° C. for 4-10 hours (5° C./min heating rate). The calcined material was finally crushed to a fine powder. 0.45 g α-$Al_2O_3$ and 50 mg of the finely ground active phase ($Mo_1V_{0.398}Ga_{1.0E-05}Pd_{1.90E-04}Nb_{0.125}Te_{0.23}$) was mixed with 500 µl water and place in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns and tested under standard reaction conditions for propane oxidation.

6. Example 4—Preparation of $Mo_1V_{0.398}Ga_{1.0E-05}Pd_{1.90E-04}Nb_{0.125}Te_{0.23}$—$LaSiO_2$ $SiO_2$ was dried overnight at 110-120° C. (5° C./min heating rate). A stock solutions of the La precursor was prepared by dissolving 0.2553 g $La(NO_3)_3$ $6H_2O$ in water using a 5.000 ml volumetric flask. The concentration of the solution was 0.05 g/mL on a metal salt basis. To 0.101 g of the $SiO_2$ was added 125 µl of the La stock solution and 375

μl water. The excess liquids were slowly removed for 8-16 hours at 110-120° C. (heating rate 5° C./min) After drying at 120° C. the modified $SiO_2$ was calcined in air at 300-500° C. for 4-10 hours (5° C./min heating rate). The calcined material was finally crushed to a fine powder. 0.45 g $SiO_2$ and 50 mg of the finely ground active phase ($Mo_1V_{0.398}Ga_{1.0E-05}Pd_{1.90E-04}Nb_{0.125}Te_{0.23}$) were mixed with 500 μl water and place in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns and tested under standard reaction conditions for propane oxidation.

7. Example 5—Preparation of $Mo_1V_{0.398}Ga_{1.0E-05}Pd_{1.90E-04}Nb_{0.125}Te_{0.23}$—$NiAl_2O_3$ $α-Al_2O_3$ was dried overnight at 110-120° (5° C./min heating rate). A stock solution of the Ni precursors was prepared by dissolving 0.2502 g $Ni(NO_3)_2 \cdot 6H_2O$ in water using a 5.000 ml volumetric flask. The concentration of the solution was 0.05 g/ml on a metal salt basis. To 0.0995 g of the $α-Al_2O_3$ was added 198 μl of the Ni stock solution and 302 μl water. The excess liquids were slowly removed for 8-16 hours at 110-120° C. (heating rate 5° C./min) After drying at 120° C. the modified $α-Al_2O_3$ were calcined in air at 300-500° C. for 4-10 hours (5° C./min heating rate). The calcined material was finally crushed to a fine powder. 0.45 g $α-Al_2O_3$ and 50 mg of the finely ground active phase ($Mo_1V_{0.398}Ga_{1.0E-05}Pd_{1.0E-04}Nb_{0.125}Te_{0.23}$) was mixed with 500 μl water and place in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns and tested under standard reaction conditions for propane oxidation.

8. Example 6—Preparation of $Mo_1V_{0.398}Ga_{10E-05}Pd_{1.90E-04}Nb_{0.125}Te_{0.23}$—$MnAl_2O_3$ $α-Al_2O_3$ was dried overnight at 120° C. (5° C./min heating rate). A stock solution of the Mn precursor was prepared by dissolving 0.2515 g $Mn(NO_3)_2 \cdot 6H_2O$ in water using a 5.000 ml volumetric flask. The concentration of the solutions was 0.05 g/mL on a metal salt basis. To 0.0995 g of the $α-Al_2O_3$ was added 183 μl of the Mn stock solution and 317 μl water. The excess liquids were slowly removed for 8-16 hours at 110-120° C. (heating rate 5° C./min). After drying at 120° C. the modified $α-Al_2O_3$ were calcined in air at 300-500° C. for 4-10 hours (5° C./min heating rate). The calcined material was finally crushed to a fine powder. 0.45 g $α-Al_2O_3$ and 50 mg of the finely ground active phase ($Mo_1V_{0.398}Ga_{1.0E-05}Pd_{1.90E-04}Nb_{0.125}Te_{0.23}$) was mixed with 500 μl water and place in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns and tested under standard reaction conditions for propane oxidation.

9. Example 7—Preparation of $Mo_1V_{0.398}Ga_{1.0E-05}Pd_{1.90E-04}Nb_{0.125}Te_{0.23}$—$TiAl_2O_3$ $α-Al_2O_3$ was dried overnight at 110-120° C. (5° C./min heating rate). A stock solutions of the Ti precursors was prepared by dissolving 0.2515 g $(CH_3CH(O)CO_2NH_4)_2Ti(OH)_2$ in water using a 5.000 ml volumetric flask. The concentration of the solutions was 0.05 g/mL on a metal salt basis. To 0.0995 g of the $α-Al_2O_3$ was added 246 μl of the Ti stock solution and 254 μl water. The excess liquids were slowly removed for 8-16 hours at 110-120° C. (heating rate 5° C./min) After drying at 120° C. the modified $α-Al_2O_3$ were calcined in air at 300-500° C. for 4-10 hours (5° C./min heating rate). The calcined material was finally crushed to a fine powder. 0.45 g $α-Al_2O_3$ and 50 mg of the finely ground active phase ($Mo_1V_{0.398}Ga_{1.0E-05}Pd_{1.90E-04}Nb_{0.125}Te_{0.23}$) was mixed with 500 μl water and placed in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns and tested under standard reaction conditions for propane oxidation.

10. Example 8—Preparation of $Mo_1V_{0.398}Ga_{1.0E-05}Pd_{1.90E-04}Nb_{0.125}Te_{0.23}$—$SbAl_2O_3$ The $α-Al_2O_3$ was dried overnight at 110-120° C. (5° C./min heating rate). A stock solution of the Sb precursor was prepared by dissolving 0.5414 g $Sb(OAc)_3$ and 1.523 g citric acid monohydrate in 3.5641 g water. The mixture was heated to 60° C. until dissolved. After cooling the density of the mixture was determined to be 1.1691 g/ml. The calculated concentration of the solution was 0.1125 g Sb-Ac/mL. It was further diluted using an additional 6.013 mL water to give a 0.05 g/mL on a metal salt basis. To 0.0495 g of the $α-Al_2O_3$ was added 49 μl of the Sb stock solution and 201 μl water. The excess liquids were slowly removed for 8-16 hours at 110-120° C. (heating rate 5° C./min) After drying at 120° C. the modified $α-Al_2O_3$ were calcined in air at 300-500° C. for 4-10 hours (5° C./min heating rate). The calcined material was finally crushed to a fine powder. 0.45 g $α-Al_2O_3$ and 50 mg of the finely ground $C_B$ phase ($Mo_1V_{0.398}Ga_{1.0E-05}Pd_{1.90E-04}Nb_{0.125}Te_{0.23}$) were mixed with 500 μl of water and place in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns and tested under standard reaction conditions for propane oxidation.

11. Example 9—Preparation of $Mo_1V_{0.398}Ga_{1.0E-05}Pd_{1.90E-04}Nb_{0.125}Te_{0.23}$—$FeAl_2O_3$ The active phase was crushed to a powder of <100 microns and used without further drying. The $α-Al_2O_3$ having a surface area of 0.75 m²/g, 0.53 ml/g pore volume, was dried overnight at 120° C. (5° C./min heating rate). A stock solution of the Fe precursor was prepared by dissolving 0.2515 g $Fe(NO_3)_3 \cdot 9H_2O$ in water using a 5.000 ml volumetric flask, The concentration of the solution was 0.05 g/mL on a metal salt basis. To 0.100 g of the $α-Al_2O_3$ was added 289 μl of the Fe stock solution and 211 μl water. The excess liquids were slowly removed for 8-16 hours at 110-120° C. (heating rate 5° C./min) After drying at 120° C. the modified $α-Al_2O_3$ was calcined in air at 300-500° C. for 4-10 hours (5° C./min heating rate). The calcined material was finally crushed to a fine powder. 0.45 g $α-Al_2O_3$ and 50 mg of the finely ground active phase ($Mo_1V_{0.398}Ga_{1.0E-05}Pd_{1.90E-04}Nb_{0.125}Te_{0.23}$) were mixed with 500 mL water and place in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns and tested under standard reaction conditions for propane oxidation.

12. Example 10—Preparation of $Mo_1V_{0.398}Ga_{1.0E-05}Pd_{1.90E-04}Nb_{0.125}Te_{0.23}$—$MnKAl_2O_3$ $\alpha$-$Al_2O_3$ was dried overnight at 110-120° C. (5° C./min heating rate). A stock solution of Mn precursors was prepared by dissolving 0.2515 g $Mn(NO_3)_2$ $6H_2O$ in water using a 5.000 ml volumetric flask. The concentration of the solutions was 0.05 g/ml on a metal salt basis. To 0.0995 g of the $\alpha$-$Al_2O_3$ was added 183 µl of the Mn stock solution and 317 µl water. The excess liquids were slowly removed for 8-16 hours at 110-120° (heating rate 5° C./min). Further, 52 µl of 0.5105 g $KNO_3$ in a 10.000 ml water solution was added to the total solids. After drying at 110-120° C., the modified $\alpha$-$Al_2O_3$ was calcined in air at 300-500° C. for 4-10 hours (5° C./min heating rate). The calcined material was finally crushed to a fine powder. 0.45 g $\alpha$-$Al_2O_3$ and 50 mg of the finely ground active phase ($Mo_1V_{0.398}Ga_{1.0E-05}Pd_{1.90E-04}Nb_{0.125}Te_{0.23}$) were mixed with 500 µl of water and place in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g of the final catalyst with a particle size of 38-425 microns, which was tested under standard reaction conditions for propane oxidation.

13. Example 11—Preparation of $Mo_1V_{0.398}Ga_{1.0E-05}Pd_{1.90E-04}Nb_{0.125}Te_{0.23}$—$TiKAl_2O_3$ $\alpha$-$Al_2O_3$ was dried overnight at 110-120° C. (5° C./min heating rate). A stock solution of the Ti precursor was prepared by dissolving 0.2515 g $(CH_3CH(O)CO_2NH_4)_2Ti(OH)_2$ in water using a 5.000 ml volumetric flask. The concentration of the solutions was 0.05 g/ml on a metal salt basis. To 0.0995 g of the $\alpha$-$Al_2O_3$ was added 246 µl of the Ti stock solution and 254 µl water. The excess liquids were slowly removed for 8-16 hours at 110-120° C. (heating rate 5° C./min) Further, 52 µl of 0.5105 g $KNO_3$ in 10.000 ml water solution was added to the total solids. After drying at 110-120° C. the modified $\alpha$-$Al_2O_3$ was calcined in air at 300-500° C. for 4-10 hours (5° C./min heating rate). The calcined material was finally crushed to a fine powder. 0.45 g $\alpha$-$Al_2O_3$ and 50 mg of the finely ground active phase ($Mo_1V_{0.398}Ga_{1.0E-05}Pd_{1.90E-04}Nb_{0.125}Te_{0.23}$) were mixed with 500 µL water and placed in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g of final catalyst with a particle size of 38-425 microns, which was tested under standard reaction conditions for propane oxidation.

14. Example 12—Preparation of $Mo_1V_{0.398}Ga_{1.0E-05}Pd_{1.90E-04}Nb_{0.125}Te_{0.23}$—$ZrAl_2O_3$ $Mo_1V_{0.398}Ga_{1.0E-05}Pd_{1.90E-04}Nb_{0.125}Te_{0.23}$ was crushed to a powder of <100 microns and used without further drying. $\alpha$-$Al_2O_3$ having a surface area of 0.75 m$^2$/g, 0.53 ml/g pore volume, was dried overnight at 120° C. (5° C./min heating rate). A stock solution of the Zr precursor was prepared by dissolving 0.2515 g $Zr(NO_3)_4$ $5H_2O$ in water using a 5.000 ml volumetric flask. The concentration of the solutions was 0.05 g/ml on a metal salt basis. To 0.10 g of the $\alpha$-$Al_2O_3$ was added 188 µl of the Zr stock solution and 312 µl water. The excess liquids were slowly removed for 8-16 hours at 110-120° C. (heating rate 5° C./min) After drying at 120° C. the modified $\alpha$-$Al_2O_3$ were calcined in air at 300-500° C. for 4-10 hours (5° C./min heating rate). The calcined material was finally crushed to a fine powder. 0.45 g $\alpha$-$Al_2O_3$ and 50 mg of the finely ground active phase ($Mo_1V_{0.398}Ga_{1.0E-05}Pd_{1.90E-04}Nb_{0.125}Te_{0.23}$) were mixed with 500 µl water and place in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g of final catalyst with a particle size of 38-425 microns, which was tested under standard reaction conditions for propane oxidation.

15. Example 13—Preparation of $Mo_1V_{0.398}Ga_{1.0E-05}Pd_{1.90E-04}Nb_{0.125}Te_{0.23}$—$CsAl_2O_3$ $Mo_1V_{0.398}Ga_{1.0E-05}Pd_{1.90E-04}Nb_{0.125}Te_{0.23}$ was crushed to a powder of <100 microns and used without further drying. The $\alpha$-$Al_2O_3$ having a surface rea of 0.75 m$^2$/g, 0.53 ml/g pore volume, was dried overnight at 120° C. (5° C./min heating rate).

A stock solution of the Cs precursor was prepared by dissolving 0.2461 g $CsNO_3$ in water using a 5.000 ml volumetric flask. The concentration of the solutions was 0.05 g/ml on a metal salt basis. To 0.10 g of the $\alpha$-$Al_2O_3$ was added 59 µl of the Cs stock solution and 441 µl water. The excess liquids were slowly removed for 8-16 hours at 110-120° C. (heating rate 5° C./min) After drying at 120° C. the modified $\alpha$-$Al_2O_3$ was calcined in air at 300-500° C. for 4-10 hours (5° C./min heating rate). The calcined material was crushed to a fine powder. 0.45 g $\alpha$-$Al_2O_3$ and 50 mg of the finely ground $Mo_1V_{0.398}Ga_{1.0E-05}Pd_{1.90E-04}Nb_{0.125}Te_{0.23}$ were mixed with 500 µl water and place in a small metal holder. Two small steel balls were used to grind the mixture in order to get a homogeneous slurry. The mixture was shaken for 30 to 120 minutes at 25 Hz. After shaking, the slurry was baked for 8-16 hours at 110° C. (5° C./min heating rate). After baking, the final material was crushed and sieved to obtain 0.4 g with a particle size of 38-425 microns and tested under standard reaction conditions for propane oxidation.

16. Catalyst Testing Experiments

The data table below lists the results of experiments that tested the catalysts of Examples 1-13 described above for propane oxidation under the standard conditions also described above. The data gives the ratio of the observed STY for total production of propylene and acrylic acid for each of catalysts 1-13 as compared to the STY for production of total propylene and acrylic acid for Experiment 14. Experiment 14 used the catalyst described in "Example $C_B$" described above, to form $Mo_1V_{0.398}Ga_{1.0E-05}Pd_{1.90E-04}Nb_{0.125}Te_{0.23}$ catalyst described in "Example $C_B$" described above, which did not add any $C_A$ to form a composite.

TABLE 1

| Activity data of exemplary composite catalyst compositions disclosed herein | | |
|---|---|---|
| | STY (propylene and acrylic acid) relative to base catalyst (Example 14 below) | |
| Example | Catalyst composition | 290° C. | 305° C. |
| 1 | MoVGaPdNbTe—Au $Al_2O_3$ | 1.26 | 1.24 |
| 2 | MoVGaPdNbTe—B $Al_2O_3$ | 1.07 | 1.12 |
| 3 | MoVGaPdNb—Ce $Al_2O_3$ | 1.24 | 1.21 |
| 4 | MoVGaPdNbTe—La $SiO_2$ | 1.46 | 1.39 |

TABLE 1-continued

Activity data of exemplary composite catalyst compositions disclosed herein

| Example | Catalyst composition | STY (propylene and acrylic acid) relative to base catalyst (Example 14 below) | |
|---|---|---|---|
| | | 290° C. | 305° C. |
| 5 | MoVGaPdNbTe—Ni Al$_2$O$_3$ | 1.18 | 1.19 |
| 6 | MoVGaPdNbTe—Mn Al$_2$O$_3$ | 1.01 | 1.07 |
| 7 | MoVGaPdNbTe—Ti Al$_2$O$_3$ | 1.07 | 1.12 |
| 8 | MoVGaPdNbTe—Sb Al$_2$O$_3$ | 1.12 | 1.12 |
| 9 | MoVGaPdNbTe—Fe Al$_2$O$_3$ | 1.07 | 1.04 |
| 10 | MoVGaPdNbTe—MnK Al$_2$O$_3$ | 1.16 | 1.24 |
| 11 | MoVGaPdNbTe—TiKAl$_2$O$_3$ | 1.15 | 1.07 |
| 12 | MoVGaPdNbTe—ZrAl$_2$O$_3$ | 1.33 | 1.26 |
| 13 | MoVGaPdNbTe—CsAl$_2$O$_3$ | 1.22 | 1.19 |
| 14 | MoVGaPdNbTe | 1.00 | 1.00 |

Figure 1B:
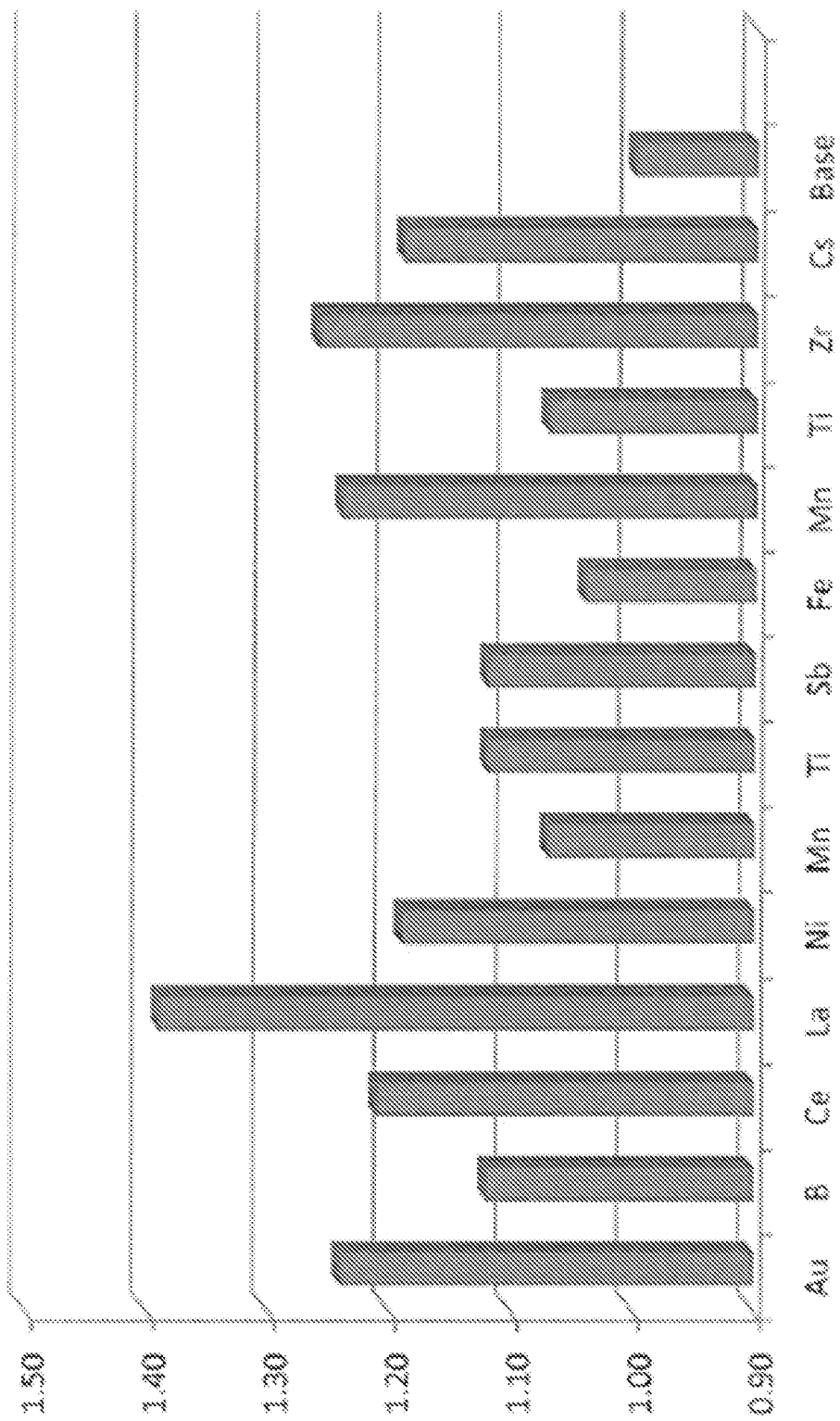

The results from Table 1 are bar graphed in FIGS. 1A and 1B, which present the results obtained at each of 290° C. (1A) and 305° C. (1B).

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A composite catalyst composition comprising CA and CB,
   a) wherein CA comprises at least components M and S, and optionally A,
      i) wherein M is at least one metal comprising B, La, Mn, Sb, Ti, Zr, Fe, Cs, Au, or Ce, or a mixture thereof;
      ii) wherein S is a support material, wherein M is dispersed over S, and
      iii) wherein A is an alkaline comprising Na, K, Mg, or Ca, or a mixture thereof; and
   b) wherein CB comprises one or more mixed metal oxide phases comprising metals in the relative molar ratios indicated by the formula Mo$_a$V$_b$Ga$_c$Pd$_d$Nb$_e$X$_f$,
      i) wherein a is 1,
      ii) wherein b is from 0.01 to 0.9,
      iii) wherein c is greater than 0 to 0.2,
      iv) wherein d is from 0.0000001 to 0.2,
      v) wherein e is greater than 0 to 0.2,
      vi) wherein X comprises La, Te, Ge, Zn, Si, In, or W, or a mixture thereof, and
      vii) wherein f is greater than 0 to 0.5, and
   c) wherein CA is present in an amount of 1% by weight to 99% by weight and CB is present in an amount of 99% by weight to 1% by weight, and
   d) wherein CB not dispersed over S.

2. The catalyst composition of claim 1, wherein A is present.

3. The catalyst composition of claim 1, wherein A is present and comprises K or Na.

4. The catalyst composition of claim 1, wherein CA is present in an amount from 20% by weight to 40% by weight and CB is present in an amount from 80% by weight to 60% by weight.

5. The catalyst composition of claim 1, wherein S comprises Al$_2$O$_3$, SiO$_2$, TiO$_2$, CeO$_2$, AlPO$_4$, ZrO$_2$, SiC, Mo-carbide, aluminumsilicate, a zeolite, or a molecular sieve, or a mixture thereof.

6. The catalyst composition of claim 1, wherein S comprises Al$_2$O$_3$ or SiO$_2$.

7. The catalyst composition of claim 1, wherein M is nano-dispersed over S.

8. The catalyst composition of claim 1, wherein S is a microporous or mesoporous material.

9. The catalyst composition of claim 1, wherein the catalyst composition has a particle size from 20 μm to 500 μm.

10. The catalyst composition of claim 1, wherein M comprises La, Zr, Ce, or Cs, or a mixture thereof.

11. The catalyst composition of claim 1, wherein M comprises La.

12. The catalyst composition of claim 1, wherein X comprises Te.

13. The catalyst composition of claim 1, wherein the catalyst composition is stable to at least 600° C.

14. The catalyst composition of claim 1, wherein the catalyst composition CA is present in an amount from 20% by weight to 40% by weight and CB is present in an amount from 80% by weight to 60% by weight, wherein A is present, wherein S comprises Al2O$_3$ or SiO$_2$ wherein M comprises La, and wherein X comprises Te.

15. A method of oxidizing a C2-C12 alkane comprising contacting a C2-C12 alkane with an oxygen containing stream and the composite catalyst composition of claim 1, thereby oxidizing the C2-C12 alkane.

16. The method of claim 15, wherein the C2-C12 alkane comprises propane.

17. The method of claim 16, wherein the oxidation produces a composition comprising acrylic acid and propylene.

18. The method of claim 17, wherein the STY for oxidation of propane to acrylic acid plus propylene is at least 40% higher relative to a reference base catalyst.

19. A method of making the composite catalyst composition of claim 1 comprising the steps of
   a) mixing a support material S with a solution comprising one or more metal compounds comprising one or more metals M comprising B, La, Mn, Sb, Ti, Zr, Fe, Cs, Au, or Ce, or a mixture thereof, and optionally one or more alkali metal compounds comprising Na, K, Mg, or Ca, or a mixture thereof, thereby dispersing the metal compounds and/or alkali metal compounds on the support material; and
   b) calcining the support material dispersed with the metal and/or alkali metal compounds to form CA;
   c) mixing CA with CB, thereby forming the catalyst composition,
      i) wherein CB comprises one or more mixed metal oxide phases comprising metals in the relative molar ratios indicated by the formula Mo$_a$V$_b$Ga$_c$Pd$_d$Nb$_e$X$_f$,
         (1) wherein a is 1,
         (2) wherein b is from 0.01 to 0.9,
         (3) wherein c is greater than 0 to 0.2,
         (4) wherein d is from 0.0000001 to 0.2,
         (5) wherein e is greater than 0 to 0.2,
         (6) wherein X comprises La, Te, Ge, Zn, Si, In, or W, or a mixture thereof, and (7) wherein f is greater than 0 to 0.5, and
ii) wherein CA is present in an amount of 1% by weight to 99% by weight and CB is present in an amount of 99% by weight to 1% by weight.

* * * * *